United States Patent [19]

Scheuble et al.

[11] Patent Number: 5,045,066
[45] Date of Patent: Sep. 3, 1991

[54] DENTAL NEEDLE WITH STICK RESISTANT PROTECTIVE SLEEVE

[75] Inventors: Gustav A. Scheuble, Des Plaines; Fritz Kohnke, Palatine; Guenther Paczka, Hoffman Estates, all of Ill.

[73] Assignee: Smith & Nephew, Inc., Largo, Fla.

[21] Appl. No.: 535,003

[22] Filed: Jun. 7, 1990

[51] Int. Cl.⁵ ............................................. A61M 5/32
[52] U.S. Cl. .................................... 604/198; 604/232; 604/263
[58] Field of Search ............... 604/198, 263, 187, 232, 604/195, 192

[56] References Cited

U.S. PATENT DOCUMENTS

| | | | |
|---|---|---|---|
| 2,925,083 | 2/1960 | Craig . | |
| 4,631,057 | 12/1986 | Mitchell | 604/198 |
| 4,655,751 | 4/1987 | Harbaugh | 604/198 |
| 4,695,274 | 9/1987 | Fox | 604/198 |
| 4,767,413 | 8/1988 | Haber et al. | 604/198 |
| 4,772,272 | 9/1988 | McFarland | 604/198 |
| 4,898,590 | 2/1990 | Andors | 604/263 X |
| 4,915,701 | 4/1990 | Halkyard | 604/232 X |
| 4,935,016 | 6/1990 | Deleo | 604/198 |

Primary Examiner—John D. Yasko
Attorney, Agent, or Firm—McDermott, Will & Emery

[57] ABSTRACT

A protective device for a dental needle is disclosed. The device comprises a generally cylindrical sleeve having therein a sliding hub assembly adapted to receive a dental syringe having a cannula with distal and proximal ends and generally rectangular openings in the walls thereof. The hub assembly includes locking means extending through the generally rectangular openings to retain the syringe in a retracted position. The sleeve extends over and covers both the distal and proximal ends of the cannula when the sleeve is in a retracted position so as to protect the dental health professional from contact with the needle.

7 Claims, 1 Drawing Sheet

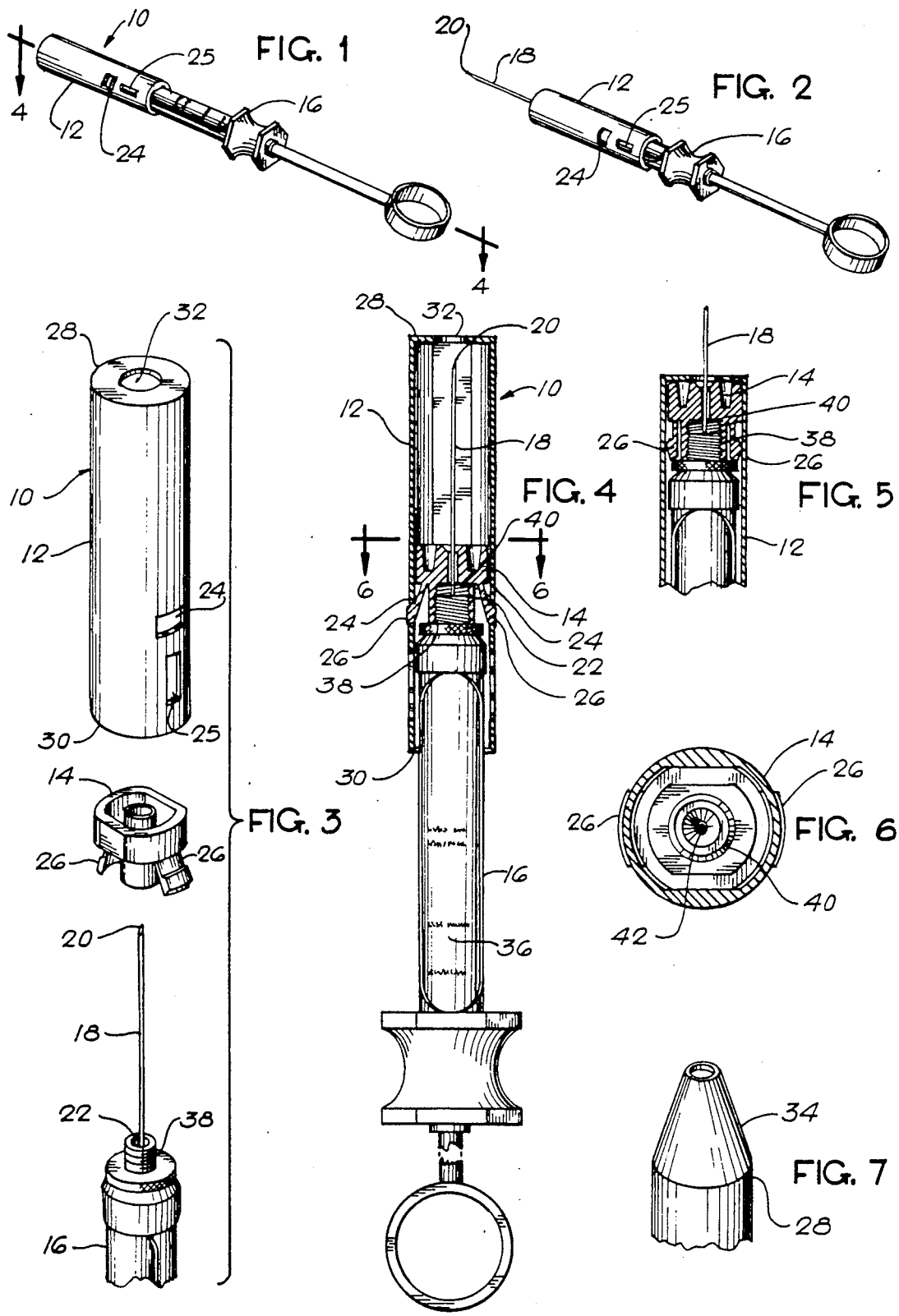

DENTAL NEEDLE WITH STICK RESISTANT PROTECTIVE SLEEVE

BACKGROUND OF THE INVENTION

The invention of this application relates to a dental needle having a stick resistant protective sleeve. More particularly, this invention relates to a protective device for a dental needle which protects the dentist from contact with the needle when giving an injection.

In recent years, the dental health professional has become increasingly aware of the hazards associated with an accidental needle stick during resheathing of the needle after an injection has been given. It has been found that numerous diseases, such as AIDS and hepatitis, can be transmitted in this fashion.

Protective sleeves for hypodermic needles have been previously suggested. McFarland, U.S. Pat. No. 4,772,272, describes a protective sleeve which overlies needle support means and a portion of the syringe in both its needle protection position and its needle injection position. The protective sleeve is positively but releasably retained in both such positions. By retaining the sleeve in the needle injection position with the needle exposed, the chances of the dental health professional being accidentally stuck with the needle are increased significantly.

Craig, U.S. Pat. No. 2,925,083, describes a hypodermic syringe having means, such as a hood, for concealing and guarding the hypodermic needle until the syringe is in position for use.

Mitchell, U.S. Pat. No. 4,631,057, describes an apparatus for injecting a substance into a human comprising a body, a needle coupled to the body and terminating in a point and a needle guard mounted on the body, for movement from a retracted position in which the guard does not shield the needle to an extended position in which the guard does shield the needle. The needle guard can be releasably retained in the retracted position and locked in the extended position. The locking of the needle guard is accomplished by interlocking members carried by the needle guard and by a collar mounted on the body.

Harbaugh, U.S. Pat. No. 4,655,751, describes a liquid dispensing and receiving syringe which includes an elongated cylindrical transparent container open at its front and rear ends and defining a central cavity for holding liquid. A rearwardly extending plunger is slideably secured in the rear end of the cavity for dispensing liquid out the front end of the container and through a hollow needle secured to the container front end for transporting liquid into the cavity from the needle. A concentric protective shell is connected to and spaced outwardly from the container sidewall and is slideable between a first needle exposing position and a second needle covering position.

Fox, U.S. Pat. No. 4,695,274, describes a safety needle attachment for a syringe body assembly which makes use of a needle holder with a needle fixed in the holder. The needle is initially surrounded by a protective jacket which is releasably interlocked with the holder. When the needle is to be used, the interlock is released and the jacket is telescoped over the holder to project the needle through a membrane over the end of the jacket to a working position.

Haber et al., U.S. Pat. No. 4,767,413, describes a disposable dental syringe having a prefilled ampule of liquid in a double-ended hypodermic needle arranged and spaced in axial alignment with the ampule. The ampule is moveable axially through the cylinder of the syringe until the proximal end of the needle penetrates the ampule and the distal end of the needle extends outwardly from the cylinder for administering an injection. The ampule is locked in the distal position so that an injection may be administered. Upon completing the injection, the ampule is released from the distal position and moved proximally through the cylinder, so that the distal end of the needle is automatically retracted within the cylinder.

Heretofore, none of the dental needles incorporating protective sleeves have adequately protected the dental health professional from accidental contact with or puncture by the needles. The invention disclosed herein comprises a protective device for a dental needle which does protect the dental health professional from contact with the needle.

SUMMARY OF THE INVENTION

The present invention contemplates a protective device for a dental needle to be administered to human subjects to protect the administrator from contact with the needle.

In one aspect of the present invention, the protective device of the invention comprises a generally cylindrical sleeve having therein a sliding hub assembly adapted to receive a dental syringe having a cannula with distal and proximal ends and generally rectangular openings in the walls thereof. The hub assembly includes locking means extending through the generally rectangular openings to retain the syringe in a retracted position so that the protective sleeve extends over and covers both the distal and proximal ends of the cannula when the sleeve is in a retracted position.

In a further aspect of the present invention, the locking means of the protective sleeve of the invention are releasable to allow the hub assembly to slide within the sleeve to thereby extend the distal end of the cannula through a centrally positioned opening in the top end of the sleeve to facilitate injection of the needle in a subject.

In another aspect of the present invention, the protective sleeve of the invention has top and bottom ends adapted to receive sealing means.

The present invention provides several benefits and advantages.

One benefit of the present invention is that the protective sleeve of the invention protects the administrator from contact with dental needles.

Another benefit of the present invention is that the ends of the protective sleeve of the invention are sealed to prevent tampering with the dental needle.

One of the advantages of the present invention is that the protective sleeve of the invention eliminates the need for the dental health professional to resheath a dental needle after its use.

Another advantage of the present invention is that the protective sleeve of the invention extends over and covers both the distal and proximal ends of the cannula or needle when the sleeve is in a retracted position and the cannula or needle is exposed only during injection.

Other benefits and advantages of the present invention will become readily apparent to those skilled in the art from the following detailed description of the invention, the drawings and the appended claims.

BRIEF DESCRIPTION OF THE DRAWINGS

In drawings forming a portion of the disclosure of this invention:

FIG. 1 is a side view of the protective device of the present invention illustrating the device in a retracted position;

FIG. 2 is a side view of the protective device of the present invention illustrating the device in position for use;

FIG. 3 is an exploded view of the protective device of the present invention;

FIG. 4 is a cross-sectional view of the protective device of FIG. 1;

FIG. 5 is a cross-sectional view of the protective device of the present invention in a use position;

FIG. 6 is a cross-sectional view of the hub assembly of the protective device of the present invention as illustrated in FIG. 4; and FIG. 7 is a front view of the top sealing means of the protective device of the present invention.

DETAILED DESCRIPTION OF THE INVENTION

The present invention is directed to a protective device for a dental needle to be administered to human subjects to protect the administrator from contact with the needle.

With reference to FIGS. 1-4, a preferred embodiment of the protective device of the present invention is shown. Protective device 10 comprises a generally cylindrical sleeve 12, constructed of a plastic material. Sleeve 12 has disposed therein a sliding hub assembly 14 which is adapted to receive a dental syringe 16 which has a cannula or needle 18 with a distal end 20, which is used for injections, and a proximal end 22. The sleeve 12 also has a plurality of horizontal, generally rectangular openings 24 and vertical, generally rectangular openings 25 in the walls thereof.

Hub assembly 14 includes a plurality of locking means or tabs 26 which extend through the generally rectangular openings 24 to thereby retain the syringe 16 in a retracted position. When the sleeve 12 and the syringe 16 are in such a retracted position, the sleeve 12 extends over and covers both the distal end 20 and the proximal end 22 of the cannula 18 to protect the dental health professional who will administer an injection with syringe 16 from any contact, accidental or otherwise, with the cannula or needle 18.

The sleeve 12 has a top end 28 and a bottom end 30. The bottom end 30 is open to the full diameter of the sleeve to permit passage of syringe 16 into sleeve 12 to engage hub assembly 14. Top end 28 has a centrally positioned opening 32 having a diameter of about one-third the diameter of the cylindrical sleeve 12.

As illustrated in FIG. 7, the top end 28 is adapted to receive a top sealing means or cap 34 which fits into centrally positioned opening 32. Cap 34 is preferably tamper indicative to maximize safety of the device to the user and patient. Bottom end 30 is also adapted to receive a bottom sealing means or cap (not shown) which is a flat, circular piece having the same outside diameter as the sleeve 12. Perpendicular to the flat portion is a circular ridge which has an outside diameter the same as the bottom inside diameter of the protective sleeve 12. Top sealing means 34 and the bottom sealing means may preferably be interconnected by a strap or other suitable connecting means.

The syringe 16 is fabricated of stainless steel, as is well known in the art, as is the cannula or needle 18. The syringe 16 has a cavity 36 adapted to receive a carpule containing the anesthetic or other medicament to be administered to a patient by injection. Cannula 18 is affixed by means of epoxy or other suitable adhesive well known to those of skill in the art to an inner sliding hub 38 which is threaded to engage hub assembly 14 at its threaded portion 40 as shown in FIGS. 4-6.

The locking means 26 of hub assembly 14 are releasable to allow hub assembly 14 to slide upwards within sleeve 12. In this manner, the distal end 20 of cannula 18 passes through an opening 42 in hub assembly 14 and is extended through centrally positioned opening 32 in the top end 28 of sleeve 12 to facilitate injection of cannula 18 in a subject or patient.

In operation, the sterile dental syringe 16, loaded in its cavity 36 with an anesthetic carpule, is inserted into the bottom end 30 of the protective sleeve 12 until it stops. The protective sleeve 12 is then rotated clockwise until threaded portion 40 is threaded onto syringe 16.

When an injection is to be made, top cap 34 is removed, then, the dental health professional holds sleeve 12 between thumb and forefinger at the point where the locking means 26 extend through the openings 24, which is about two-thirds of the length of sleeve 12, from top end 28 to bottom end 30. The locking means 26 are then depressed releasing hub assembly 14. The syringe 16 is pushed through sleeve 12 to extend needle 18 through opening 32 and the injection is made.

When the injection is complete, the protective sleeve 12 is held firmly by the dental health professional between thumb and forefinger. The syringe 16 is pulled back to retract needle 18 until locking means 26 are in their original position extending through openings 24 to lock sleeve 12 in a retracted position. While still holding protective sleeve 12, the dental health professional rotates sleeve 12 counter-clockwise until inner hub 38 disengages from threaded portion 40 of hub assembly 14. Needle 18 is then removed from syringe 16 and disposed of by means well known in the art.

The protective device of the present invention, when used properly as described above, virtually eliminates the possibility of the dental health professional sticking himself or herself during resheathing of the needle.

The foregoing is intended as illustrative of the present invention but not limiting. Numerous variations and modifications may be effected without departing from the true spirit and scope of the invention.

What is claimed is:

1. A protective device for a dental needle to be administered to human subjects to protect the administrator from contact with said needle comprising a generally cylindrical sleeve having therein a sliding hub assembly adapted to receive a dental syringe, said syringe having a cannula with distal and proximal ends and a cavity for receiving a carpule, said sleeve also having generally rectangular openings in the walls thereof, said hub assembly including releasable locking means extending through said generally rectangular openings to releasably retain said syringe in a retracted position, said sleeve extending over and covering both said distal and proximal ends of said cannula when said sleeve is in a retracted position.

2. The protective device of claim 1 wherein said sleeve has a top end and a bottom end, said bottom end being open to permit passage of said syringe to engage said hub assembly.

3. The protective device for claim 2 wherein said top end of said sleeve has a centrally positioned opening therein.

4. The protective device of claim 3 wherein said hub assembly is adapted to slide within said sleeve to thereby extend said distal end of said cannula through said centrally positioned opening to facilitate injection of said needle in a subject.

5. The protective device of claim 4 wherein said centrally positioned opening is adapted to receive top sealing means, said top sealing means being tamper indicative.

6. The protective device of claim 1 wherein said sleeve is fabricated of a plastic material.

7. The protective device of claim 1 wherein said dental syringe is fabricated of stainless steel.

* * * * *